(12) United States Patent
Suzuki (10) Patent No.: US 10,612,533 B2
(45) Date of Patent: Apr. 7, 2020

(54) RECIPROCATION PUMP AND A DIALYSIS APPARATUS EQUIPPED WITH THE RECIPROCATION PUMP

(75) Inventor: Hiroaki Suzuki, Makinohara (JP)

(73) Assignee: Nikkiso Company Limited, Tokyo (JP)

( * ) Notice: Subject to any disclaimer, the term of this patent is extended or adjusted under 35 U.S.C. 154(b) by 430 days.

(21) Appl. No.: 13/479,404

(22) Filed: May 24, 2012

(65) Prior Publication Data
US 2012/0282118 A1 Nov. 8, 2012

Related U.S. Application Data

(63) Continuation of application No. PCT/JP2010/070827, filed on Nov. 22, 2010.

(30) Foreign Application Priority Data

Nov. 24, 2009 (JP) ................................ 2009-266394

(51) Int. Cl.
*F04B 23/06* (2006.01)
*F04B 3/00* (2006.01)
(Continued)

(52) U.S. Cl.
CPC ............... *F04B 23/06* (2013.01); *A61M 1/14* (2013.01); *A61M 1/1639* (2014.02);
(Continued)

(58) Field of Classification Search
CPC ............... F04B 25/005; F04B 27/0423; F04B 27/0478; F04B 43/02; F04B 43/025;
(Continued)

(56) References Cited

U.S. PATENT DOCUMENTS 3,288,036 A * 11/1966 Fisher ............................... 92/62
4,470,771 A *  9/1984 Hall ....................... F04B 9/1178
                                                            417/342
(Continued)

FOREIGN PATENT DOCUMENTS

DE          2408119         8/1974
JP          50-24675        3/1975
(Continued)

*Primary Examiner* — Bryan M Lettman
*Assistant Examiner* — Charles W Nichols
(74) *Attorney, Agent, or Firm* — Harness, Dickey & Pierce, P.L.C.

(57) ABSTRACT

A reciprocation pump has a supply liquid-side sub-pumping chamber and a waste liquid side sub-pumping chamber for containing and sending out liquid adapted to communicate with the supply liquid-side pumping chamber and with the waste liquid-side pumping chamber, respectively. The supply liquid-side sub-pumping chamber and the waste liquid-side sub-pumping chamber are interlocked with a reciprocation mechanism to vary their volume reversely to that of the volume variation of the supply liquid-side pumping chamber and the waste liquid-side pumping chamber, respectively. The reciprocating motion of the reciprocation mechanism enables the liquid to be supplied to the objective apparatus through the supply liquid-side pumping chamber and the supply liquid-side sub-pumping chamber. Also, it enables the waste liquid from the objective apparatus to be discharged to the outside through the waste liquid-side pumping chamber and the waste liquid-side sub-pumping chamber.

11 Claims, 9 Drawing Sheets

(51) Int. Cl.
  *F04B 9/02* (2006.01)
  *A61M 1/14* (2006.01)
  *A61M 1/16* (2006.01)
  *F04B 11/00* (2006.01)
  *F04B 43/02* (2006.01)
  *F04B 13/02* (2006.01)

(52) U.S. Cl.
  CPC ............. *A61M 1/1641* (2014.02); *F04B 3/00* (2013.01); *F04B 9/02* (2013.01); *F04B 11/0075* (2013.01); *F04B 13/02* (2013.01); *F04B 43/025* (2013.01); *F04B 43/026* (2013.01)

(58) Field of Classification Search
  CPC .... F04B 43/026; F04B 45/043; F04B 45/047; F04B 37/00; F04B 39/12; F04B 41/06; F04B 11/005; F04B 11/0075; F04B 11/0091; A61M 1/1639; A61M 1/1641
  USPC ......... 417/244, 250, 251, 267, 410.1, 413.1; 210/646; 92/48, 146, 151
  See application file for complete search history.

(56) References Cited

U.S. PATENT DOCUMENTS

| | | | |
|---|---|---|---|
| 4,600,365 A | | 7/1986 | Riggenmann |
| 4,676,905 A | * | 6/1987 | Nagao et al. ................. 210/646 |
| 4,761,118 A | * | 8/1988 | Zanarini ....................... 417/254 |
| 4,857,199 A | * | 8/1989 | Cortial .................... A61M 1/16 210/101 |
| 5,279,504 A | * | 1/1994 | Williams ...................... 417/393 |
| 5,961,300 A | * | 10/1999 | Pitzer .................. F04B 43/0736 417/393 |
| 2004/0164013 A1 | | 8/2004 | Takao et al. |
| 2005/0254971 A1 | * | 11/2005 | Ohya et al. ................. 417/413.1 |
| 2009/0038684 A1 | * | 2/2009 | Chatfield .............. F01C 21/006 137/1 |
| 2012/0291896 A1 | * | 11/2012 | Shade ...................... 137/599.01 |

FOREIGN PATENT DOCUMENTS

| | | |
|---|---|---|
| JP | 2003-003966 | 1/2003 |
| JP | 2003-284772 | 10/2003 |
| JP | 50-4304 | 8/2012 |

\* cited by examiner

RECIPROCATION PUMP AND A DIALYSIS APPARATUS EQUIPPED WITH THE RECIPROCATION PUMP

CROSS-REFERENCE TO RELATED APPLICATIONS

This application is a continuation of International Application No. PCT/JP2010/070827, filed Nov. 22, 2010, which claims priority to Japanese Application No. 2009-266394, filed Nov. 24, 2009. The disclosures of the above applications are incorporating herein by reference.

FIELD

The present disclosure relates to a reciprocation pump, including a supply liquid-side pumping chamber and a water liquid-side pumping chamber, for supplying a liquid from a source through the supply liquid-side pumping chamber to an objective apparatus and discharging waste liquid from the objective apparatus through the waste liquid-side pumping chamber to the outside and to a dialysis apparatus equipped with the reciprocation pump.

BACKGROUND

In general, a blood purification apparatus, such as a dialyzer, is used in hemodialysis treatment. A dialysate supply line, for supplying the dialysate, as well as a dialysate discharge line, for discharging the waste dialysate, are connected to the blood purification apparatus. The dialysate supply line and dialysate discharge line extend from a dialysis apparatus main body. The lines connect to the blood purification apparatus to supply the dialysate to the blood purification apparatus and to discharge the waste dialysate from the blood purification apparatus to the outside.

The reciprocation pump (duplex pump) is connected to the dialysis apparatus main body across the dialysate supplying line and the dialysate discharging line. As shown, for example in Patent Document 1, the reciprocation pump includes a casing, for reciprocatably accommodating a plunger, a supply liquid-side pumping chamber and a waste liquid-side pumping chamber, formed by a plunger within the casing, and a motor M for reciprocating the plunger.

The supply liquid-side pumping chamber and the waste liquid-side pumping chamber include a suction valve and a discharge valve formed as check valves. The reciprocation pump is structured so that the supply liquid-side pumping chamber supplies dialysate to a blood purification apparatus. The waste liquid-side pumping chamber discharges waste dialysate from the blood purification apparatus to the outside. This is performed by the reciprocating motion of the plunger driven by a motor. See, Japanese Laid-open Patent Publication No. 2003-284772.

However, in prior art reciprocation pump, it is necessary to increase the volume of a mixing chamber arranged at a dialysate conditioning section for mixing clean water for dialysis and stock dialysate due to the pulsation caused by reciprocating motion of the plunger. In addition, it is believed that the pulsation caused by the reciprocating motion of the plunger would be excessively large. Thus, various undesirable problems would be caused when trying to supply a large amount of dialysate to the blood purification apparatus. That is, an increase in the flow rate of the dialysate would cause an increase of the internal pressure within dialysate pipes due to their flow resistance. Thus, it is necessary that the piping elements in various piping sections should be adapted to high pressure when trying to supply a large amount of dialysate to the blood purification apparatus. These problems will be similarly encountered in reciprocation pumps that supply liquids to objective apparatus in fields other than dialysis.

SUMMARY

It is, therefore, an object of the present disclosure to provide a reciprocation pump that can reduce the pulsation of the liquid and waste liquid caused by the reciprocating motion of the reciprocation pump. Also, it is an object to provide a dialysis apparatus equipped with such a reciprocation pump.

According to the present disclosure, a reciprocation pump comprises a supply liquid-side pumping chamber to supply liquid from a source to an objective apparatus. A waste liquid-side pumping chamber discharges a waste liquid from the objective apparatus to the outside. A reciprocation mechanism is able to reciprocate between the supply liquid-side pumping chamber and the waste liquid-side pumping chamber. The reciprocating motion of the reciprocation mechanism performs the suction and discharge of the liquid to and from the supply liquid-side pumping chamber. Additionally, the reciprocation mechanism performs the suction and discharge of the waste liquid to and from the waste liquid-side pumping chamber. A driving source drives the reciprocation mechanism. The reciprocation pump is adapted to supply the liquid from the source to the supply liquid-side pumping chamber of the objective apparatus. Also, it discharges the waste liquid from the waste liquid-side pumping chamber of the objective apparatus to the outside. The reciprocation pump further comprises a supply liquid-side sub-pumping chamber. The sub-pumping chamber contains and sends out liquid adapted to communicate with the supply liquid-side pumping chamber. The sub-pumping chamber is also interlocked with the reciprocation mechanism to vary its volume reversely to that of the volume variation of the supply liquid-side pumping chamber. A waste liquid-side sub-pumping chamber contains and sends out liquid adapted to communicate with the waste liquid-side pumping chamber. The waste liquid side sub-pumping chamber is interlocked with the reciprocation mechanism to vary its volume reversely to that of the volume variation of the waste liquid-side pumping chamber. The reciprocating motion of the reciprocation mechanism enables the liquid to be supplied to the objective apparatus through the supply liquid-side pumping chamber and the supply liquid-side sub-pumping chamber. Also, the reciprocation motion enables the waste liquid to be discharged from the objective apparatus to the outside through the waste liquid-side pumping chamber and the waste liquid-side sub-pumping chamber.

The reciprocation pump further comprises a rod extending through the supply liquid-side sub-pumping chamber, the supply liquidside pumping chamber, the waste liquid-side pumping chamber and the waste liquid-side sub-pumping chamber. The rod is connected to the reciprocation mechanism and the driving source to transmit a driving force from the driving source to the reciprocation means. Diaphragms, respectively mounted on the distal end and the proximal end of the rod along with the casing, form the supply liquid-side sub-pumping chamber and the waste liquid-side sub-pumping chamber, respectively.

The order of flow is arbitrary selected through the supply liquid-side pumping chamber and the supply liquid-side sub-pumping chamber. Also, the order of flow is arbitrarily selected through the waste liquid-side pumping chamber and the waste liquid-side sub-pumping chamber. This arbitrarily selected flow arbitrarily controls pulsation caused by the reciprocating motion of the reciprocation mechanism.

The reciprocation mechanism includes a plunger formed on the rod to form the supply liquid-side pumping chamber and the waste liquid-side pumping chamber.

The reciprocation mechanism includes a diaphragm mounted on the rod to form the supply liquid-side pumping chamber and the waste liquid-side pumping chamber.

The objective apparatus is a blood purification apparatus and the liquid is dialysate.

The dialysis apparatus is equipped with the above described reciprocation pump.

The reciprocation pump is provided with the supply liquid-side sub-pumping chamber and the waste liquid-side sub-pumping chamber. This is in addition to the supply liquid-side pumping chamber and the waste liquid-side pumping chamber. Thus, the pump is structured so that the reciprocating motion of the reciprocation mechanism enables the liquid to be supplied to the objective apparatus through the supply liquid-side pumping chamber and the supply liquid-side sub-pumping chamber. Also, the waste liquid from the objective apparatus is discharged to the outside through the waste liquid-side pumping chamber and the waste liquid-side sub-pumping chamber. Accordingly, it is possible to reduce the pulsation of the liquid and waste liquid caused by the reciprocating motion of the reciprocation pump.

The reciprocation pump further comprises a rod extending through the supply liquid-side sub-pumping chamber, the supply liquid-side pumping chamber, the waste liquid-side pumping chamber and the waste liquid-side sub-pumping chamber. The rod is connected to the reciprocation mechanism and the driving source to transmit a driving force from the driving source to the reciprocation mechanism. Diaphragms, respectively mounted on the distal end and the proximal end of the rod along with the casing, form the supply liquid-side sub-pumping chamber and the waste liquid-side sub-pumping chamber, respectively. Thus, it is possible to construct the supply liquid-side sub-pumping chamber, interlocked with the reciprocation mechanism, to vary its volume reversely to that of the volume variation of the supply liquid-side pumping chamber. Additionally, the waste liquid-side sub-pumping chamber, interlocked with the reciprocation mechanism, varies its volume reversely to that of the volume variation of the waste liquid-side pumping chamber. Further, any separate sealing mechanisms, such as shaft seals at mounting portions of the diaphragms, are eliminated.

The order of flow of the dialysate through the supply liquid-side pumping chamber and the supply liquid-side sub-pumping chamber and/or the order of flow of the waste dialysate through the waste liquid-side pumping chamber and the waste liquid-side sub-pumping chamber is arbitrarily selectable to arbitrarily control pulsation caused by the reciprocating motion of the reciprocation mechanism. Thus, it is possible to set the pulsation at an arbitral position of the pump to have a desirable flow rate waveform.

The reciprocation mechanism comprises a plunger formed on the rod to form the supply liquid-side pumping chamber and the waste liquid-side pumping chamber. Thus, it is possible to use a conventional plunger and to reduce the manufacturing cost.

The reciprocation mechanism comprises a diaphragm mounted on the rod to form the supply liquid-side pumping chamber and the waste liquid-side pumping chamber. Thus, it is possible to eliminate any sealing elements for forming the supply liquid-side pumping chamber and the waste liquid-side pumping chamber in a sealed manner as compared with a case using a plunger for this purpose.

The objective apparatus is a blood purification apparatus and the liquid is dialysate. Thus, it is possible to reduce the pulsation of the liquid and waste liquid caused by the reciprocating motion of the reciprocation pump. Thus, it is possible to provide a dialysis apparatus having superior effects of the reciprocation pump defined above.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 5(a-c) are graphs showing the pulsation under the first condition of connection of the reciprocation pump of FIG. 1;

FIGS. 8 (a-c) are graphs showing the pulsation under the third condition of connection of the reciprocation pump of FIG. 1.

DETAILED DESCRIPTION

The preferable embodiments of the present disclosure will be described with reference to the accompanied drawings.

Figure 1:
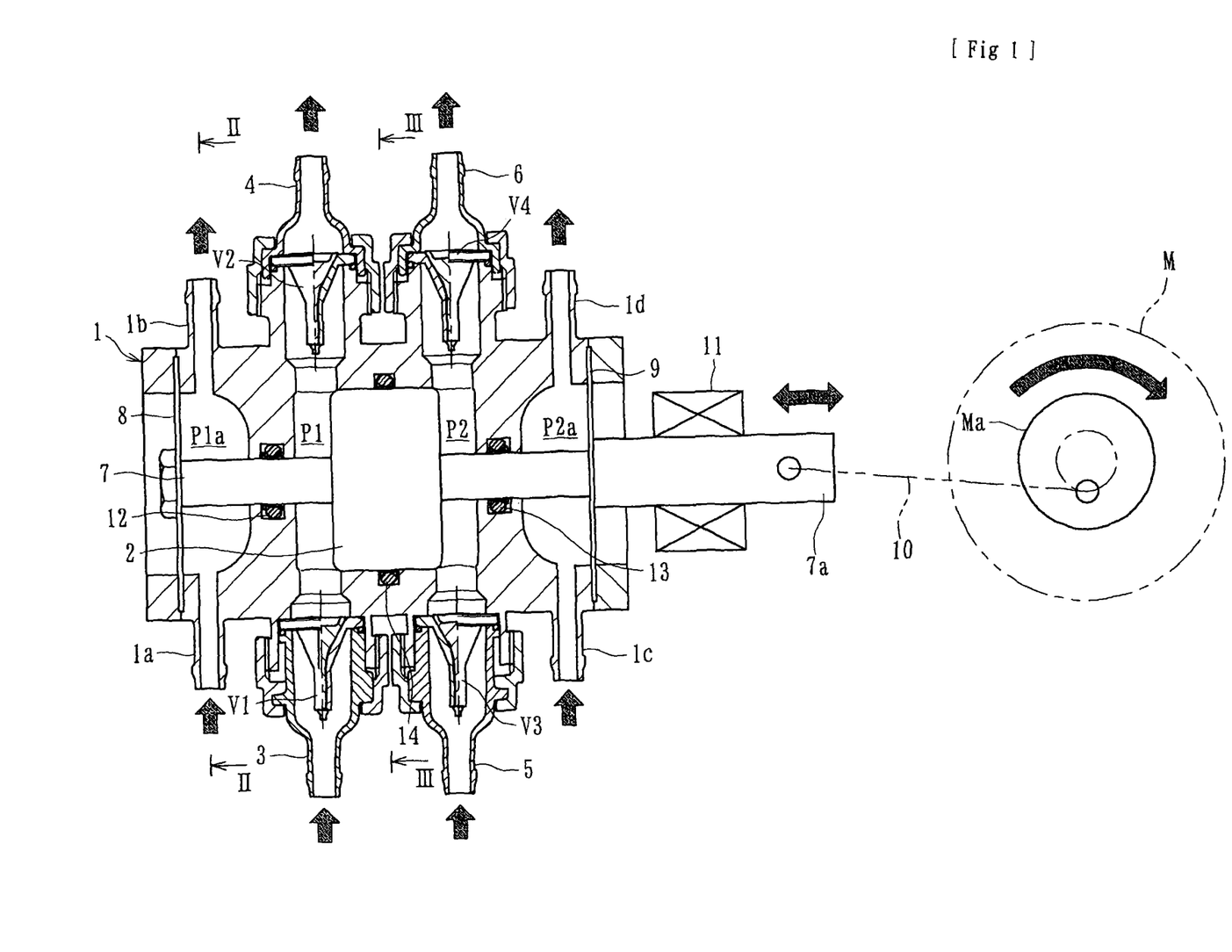
FIG. 1 is a longitudinal-section view of a reciprocation pump of the present disclosure.
Figure 2:
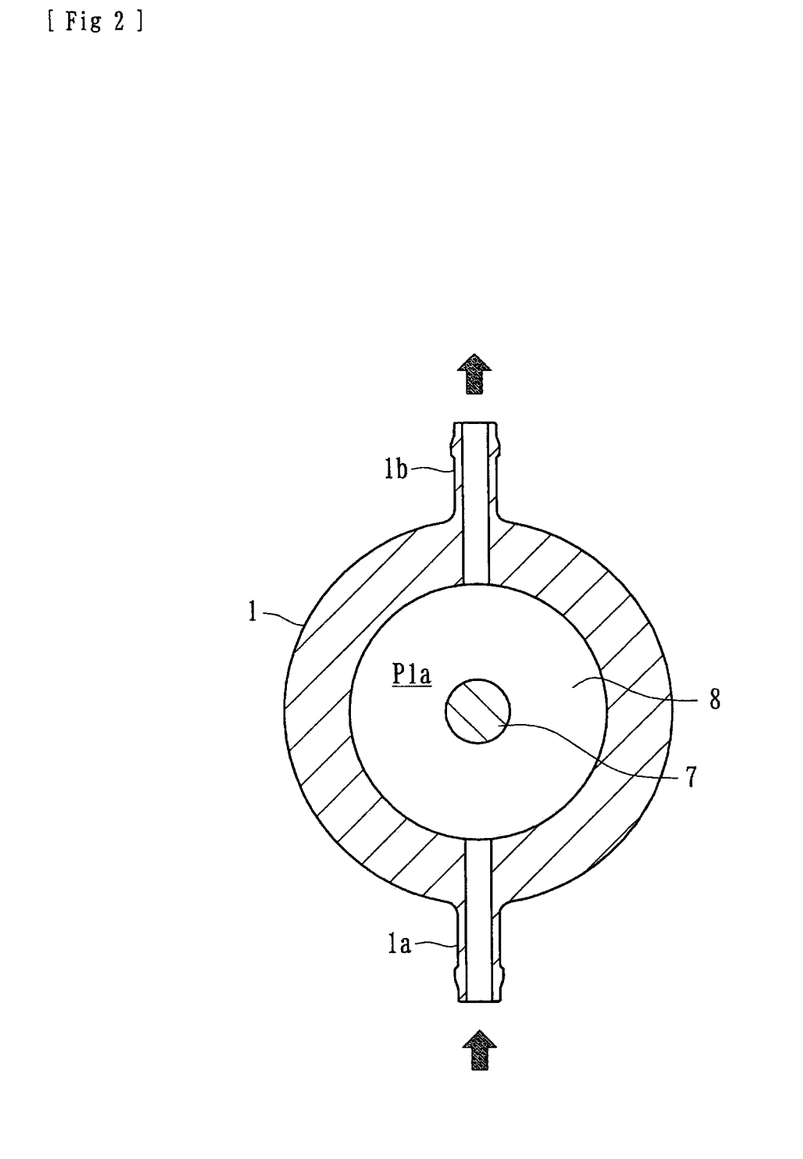
FIG. 2 is a cross-sectional view taken along a line II-II of FIG. 1.
Figure 3:
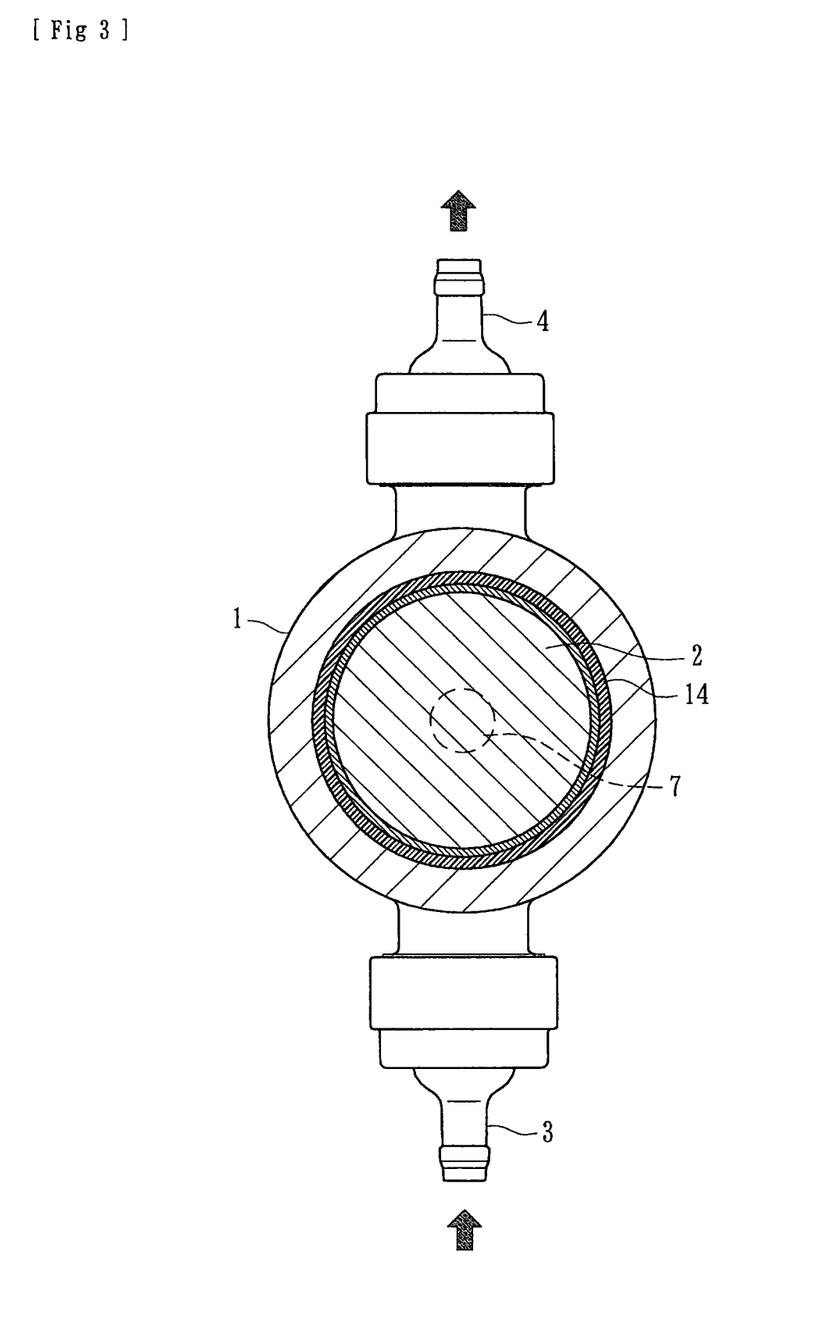
FIG. 3 is a cross-sectional view taken along a line II'-III of FIG. 1.

The reciprocation pump of one embodiment of the present disclosure can be applied to the hemodialysis apparatus and include a so-called duplex pump to supply a liquid to a supply liquid-side pumping chamber and to discharge waste liquid from a waste liquid-side pumping chamber of an objective apparatus. As shown in FIGS. 1-3, the reciprocation pump of the present disclosure includes a casing 1, a supply liquid-side pumping chamber P1, a waste liquid-side pumping chamber P2, a plunger 2, a supply liquid-side sub-pumping chamber P1a, a diaphragm 8, a waste liquid-side sub-pumping chamber P2a, a diaphragm 9, a rod 7, a motor M, sealing means 12, 13, and a central sealing means 14.

Figure 4:
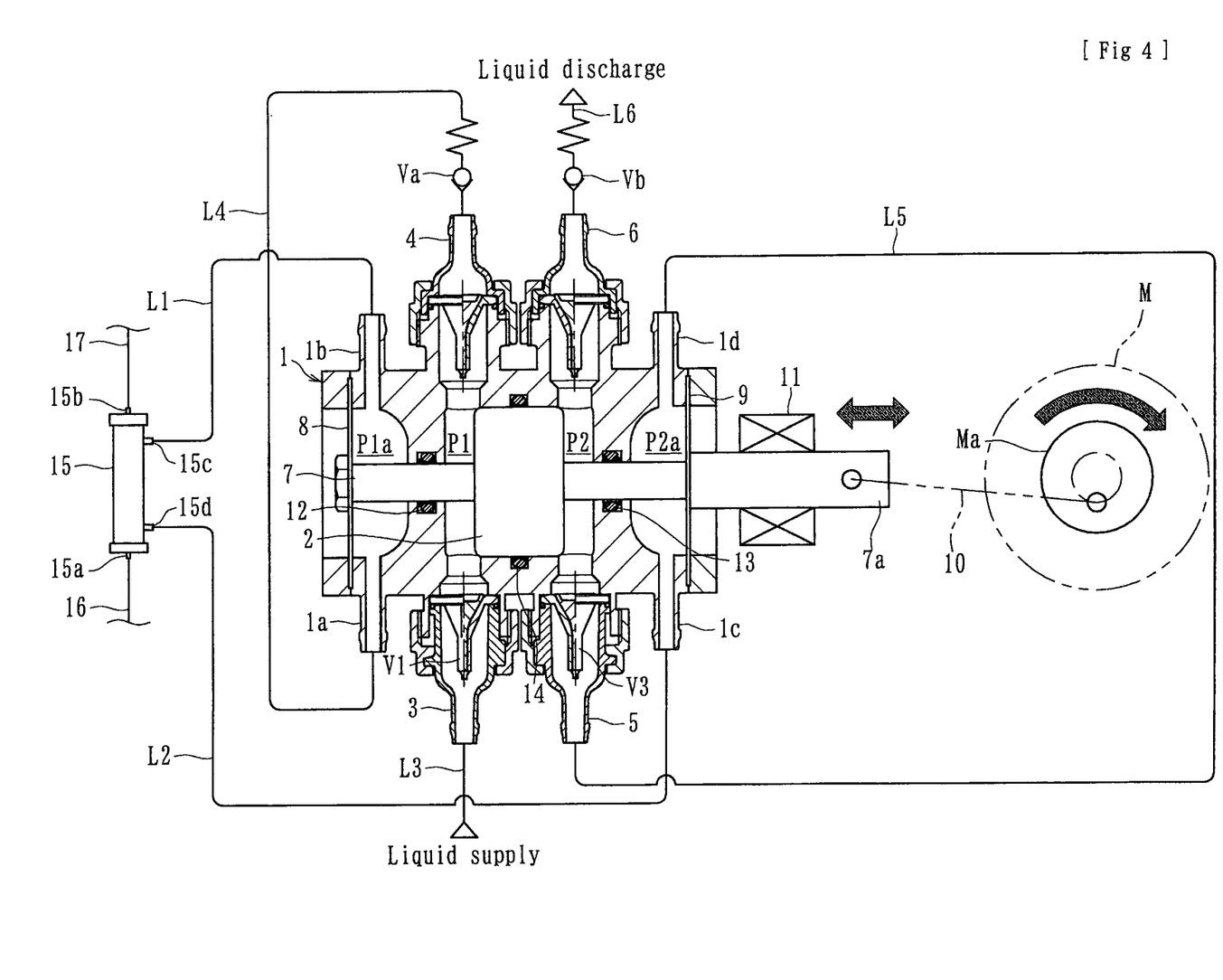
FIG. 4 is a schematic view illustrating a connection (first condition of connection) between the reciprocation pump and a blood purification apparatus.

As shown in FIG. 4, the reciprocation pump is connected to the objective apparatus, acting as a blood purification apparatus 15. The blood purification apparatus 15 is formed with a blood inlet port 15a, a blood outlet port 15b, dialysate inlet port 15c, and dialysate outlet port 15d. An arterial blood circuit 16 is connected to the blood inlet port 15a and a venous blood circuit 17 is connected to the blood outlet port 15b. In addition, a dialysate supplying line L1, extending from the reciprocation pump. is connected to a dialysate inlet port 15c. A dialysate discharge line L2, extending from the reciprocation pump, is connected to a dialysate outlet port 15d.

The arterial blood circuit 16 and the venous blood circuit 17 form a blood circuit for extracorporeally circulating blood from a patient and are respectively equipped with an arterial puncture needle and a venous puncture needle (not shown). The blood purification apparatus 15 contains an enormous number of hollow fiber membranes (blood purification membranes). The inside of each hollow fiber membrane communicates with the blood inlet port 15a and the blood outlet port 15b and forms a blood flow route. On the other hand, a space between the outer circumferential surface of each hollow fiber membrane and the inner circumferential surface of the casing of the blood purification apparatus 15 communicates with the dialysate inlet port 15c and the dialysate outlet port 15d. This forms the dialysate flow route to pass the dialysate (liquid) supplied by the reciprocation pump. Since the hollow fiber membrane is formed with an enormous number of micro pores, unnecessary materials (blood waste materials) can be removed by dialysate via the hollow fiber membranes.

The casing 1 of the reciprocation pump of the present disclosure is formed from metallic parts or molded hard plastic parts. The supply liquid-side pumping chamber P1, the waste liquid-side pumping chamber P2, the supply liquid-side sub-pumping chamber P1a, and the waste liquid-side sub-pumping chamber P2a are all formed in the casing 1. Projected connection ports 1a, 1b are formed on the casing 1 at the bottom and top of the supply liquid-side sub-pumping chamber P1a. Appropriate flow routes (e.g. flexible tubes) are connected thereto. Similarly, projected connection ports 1c, 1d are formed on the casing 1 at the bottom and top of the waste liquid-side sub-pumping chamber P2a. Also, appropriate flow routes (e.g. flexible tubes) are connected thereto.

The supply liquid-side pumping chamber P1 is intended to supply the dialysate to the blood purification apparatus 15 (FIG. 4). A supply liquid-side inlet port 3 and a supply liquid-side outlet port 4 are arranged at the bottom and top of the supply liquid-side pumping chamber P1. Reference characters V1, V2 denote check valves that are mounted, respectively, on the supply liquid-side inlet port 3 and the supply liquid-side outlet port 4. The check valves V1, V2 act to permit flow of the dialysate from the bottom to the top and to prevent flow of the dialysate from the top to the bottom of the supply liquid-side pumping chamber P1.

The waste liquid-side pumping chamber P2 is intended to discharge a waste liquid to the outside of the reciprocation pump. A waste liquid-side inlet port 5 and a waste liquid-side outlet port 6 are arranged at the bottom and top of the waste liquid-side pumping chamber P2. Reference characters V3, V4 denote check valves that are mounted, respectively, on the waste liquid-side inlet port 5 and the waste liquid-side outlet port 6. The check valves V3, V4 act to permit flow of the waste liquid from the bottom to the top and prevent flow of the waste liquid from the top to the bottom of the waste liquid-side pumping chamber P2.

The plunger 2 can be reciprocated between the supply liquid-side pumping chamber P1 and the waste liquid-side pumping chamber P2. The motor M acts as a driving source. The plunger 2 performs the suction and discharge of the dialysate to and from the supply liquid-side pumping chamber P1 and the suction and discharge of the waste dialysate to and from the waste liquid-side pumping chamber P2. That is, the suction of the dialysate from its source and the supply of the dialysate to the blood purification apparatus 15 are repeatingly performed in the supply liquid-side pumping chamber P1. Also, the suction of the waste dialysate from the blood purification apparatus 15 and the discharge of the waste dialysate to the outside of the reciprocation pump are repeatingly performed in the waste liquid-side pumping chamber P2 and are simultaneously and repeatingly performed in the waste liquid-side pumping chamber P2 during reciprocal motion of the plunger 2.

The supply liquid-side sub-pumping chamber P1a is arranged adjacent to the supply liquid-side pumping chamber P1 at the external side (left-side). The supply liquid-side sub-pumping chamber P1a is formed by the diaphragm 8 mounted on the rod 7. It is adapted to perform the suction and discharge of the dialysate via the connection ports 1a, 1b. The diaphragm 8 is secured to the casing 1 by its peripheral edge being fit into the casing, via a sealed manner. The diaphragm is adapted to be displaced by the rod 7 to vary the volume of the supply liquid-side sub-pumping chamber P1a.

The waste liquid-side sub-pumping chamber P2a is arranged adjacent to the waste liquid-side pumping chamber P2 at the external side (right-side). The waste liquid-side sub-pumping chamber P2a is formed by the diaphragm 9 mounted on the rod 7. It is adapted to perform the suction and discharge of the waste dialysate via the connection ports 1c, 1d. The diaphragm 9 is secured to the casing 1 by its peripheral edge being fit into the casing, via a sealed manner. The diaphragm 9 is adapted to be displaced by the rod 7 to vary the volume of the waste liquid-side sub-pumping chamber P2a.

The rod 7 extends through the supply liquid-side sub-pumping chamber P1a, the supply liquid-side pumping chamber P1, the waste liquid-side pumping chamber P2 and the waste liquid-side sub-pumping chamber P2a. The rod 7 is connected to the plunger 2 (reciprocation mechanism) and the motor M (driving source) to transmit a driving force of the motor M to the plunger 2 and to reciprocate the plunger 2. More particularly, diaphragms 8, 9 are mounted, respectively, on the distal end and the proximal end of the rod 7. The plunger 2 is also mounted on the rod 7 at a substantially central position between the diaphragms 8, 9.

The supply liquid-side sub-pumping chamber P1a can communicate with the supply liquid-side pumping chamber P1 so that it permits the dialysate to flow therethrough. The diaphragm 8 is interlocked with the plunger 2 and varies the volume of the supply liquid-side sub-pumping chamber P1a reversely to the volume variation of the supply liquid-side pumping chamber P1. Thus, the volume of the supply liquid-side sub-pumping chamber P1a is reduced in accordance with an increase of the volume of the supply liquid-side pumping chamber P1. On the contrary, the volume of the supply liquid-side sub-pumping chamber P1a is increased in accordance with a reduction of the volume of the supply liquid-side pumping chamber P1. Similarly, the waste liquid-side sub-pumping chamber P2a can communicate with the waste liquid-side pumping chamber P2 so that it permits the waste dialysate to flow therethrough. The diaphragm 9 is interlocked with the plunger 2 and varies the volume of the waste liquid-side sub-pumping chamber P2a reversely to the volume variation of the waste liquid-side pumping chamber P2. Thus, the volume of the waste liquid-side sub-pumping chamber P2a is reduced in accordance with an increase of the volume of the waste liquid-side pumping chamber P2. On the contrary, the volume of the waste liquid-side sub-pumping chamber P2a is increased in accordance with a reduction of the volume of the waste liquid-side pumping chamber P2.

As shown in FIG. 1, a crosshead 7a is mounted on the proximal end of the rod 7. The crosshead 7a is received in a crosshead cylinder 11 to guide the reciprocal motion of the rod 7. An output shaft Ma, of the motor M, is connected to the crosshead 7a, via a connecting rod 10. Thus, the rod 7 can be reciprocated by the rotation of the motor M via the connecting rod 10.

Sealing elements 12, 13 are sealing parts in common use, such as O-rings. The sealing elements 12, 13 are arranged, respectively, in walls through which the rod 7 extends. The sealing elements 12, 13 partition the supply liquid-side pumping chamber P1 and the supply liquid-side sub-pumping chamber P1a as well as the waste liquid-side pumping chamber P2 and the waste liquid-side sub-pumping chamber P2a. The sealing elements 12, 13 enable the reciprocal sliding motion of the rod 7 while preventing leakage of the liquid between the supply liquid-side pumping chamber P1 and the supply liquid-side sub-pumping chamber P1a as well as the waste liquid-side pumping chamber P2 and the waste liquid-side sub-pumping chamber P2a.

A central sealing element 14, also a sealing part in common use such as an O-ring, is arranged between the supply liquid-side pumping chamber P1 and the waste liquid-side pumping chamber P2. The sealing element 14 is substantially at a reciprocating center of the plunger 2 to seal the supply liquid-side pumping chamber P1 and the waste liquid-side pumping chamber P2 from each other. That is, the supply liquid-side pumping chamber P1 is sealed by the sealing element 12 and the central sealing element 14. The waste liquid-side pumping chamber P2 is sealed by the sealing element 13 and the central sealing element 14.

The dialysate is supplied to the blood purification apparatus 15 via both the supply liquid-side pumping chamber P1 and the supply liquid-side sub-pumping chamber P1a. The waste dialysate is discharged from the blood purification apparatus 15 via both the waste liquid-side pumping chamber P2 and the waste liquid-side sub-pumping chamber P2a. As shown in FIG. 4, the dialysate supplying line L1 is connected between the dialysate inlet port 15c of the blood purification apparatus 15 and the projected connection port 1b. The dialysate discharge line L2 is connected between the dialysate discharging port 15d of the blood purification apparatus 15 and the projected connection port 1c. This connection, shown in FIG. 4, is hereinafter referred to as "first condition of connection.

In the first condition of connection, a flow route L4, forming part of the dialysate supplying line L1, is connected between the projected connection port 1a and the supply liquid-side outlet port 4. The supply liquid-side inlet port 3 is connected to a flow route L3 that forms part of the dialysate supplying line L1. The flow route L3 is further connected to the supplying source (not shown) of the dialysate conditioned to a predetermined concentration. Thus, the dialysate fed from the supplying source can be supplied to the blood purification apparatus 15 through the supply liquid-side pumping chamber P1 and the supply liquid-side sub-pumping chamber P1a.

On the other hand, a flow route L5, forming part of the dialysate discharge line L2, is connected to the projected connection port 1d and the waste liquid-side inlet port 5. The waste liquid-side outlet port 6 is connected to a flow route L6 that forms part of the dialysate discharge line L2. The flow route L6 is connected to any discharged liquid recovering means (not shown). Thus, the discharged liquid from the blood purification apparatus 15 can be recovered by the discharged liquid recovering mechanism through the waste liquid-side sub-pumping chamber P2a and the waste liquid-side pumping chamber P2. Reference characters Va, Vb in FIG. 4 denotes back pressure valves connected respectively to the flow route L4, L6.

When the plunger 2 is moved by the motor M toward the right in FIG. 4, the dialysate is sucked into the supply liquid-side pumping chamber P1 from the dialysate supplying source. Simultaneously, the diaphragm 8 is also pulled and deflected toward the right. This reduces the volume of the supply liquid-side sub-pumping chamber P1a. Thus, the dialysate is supplied to the blood purification apparatus 15 from the supply liquid-side sub-pumping chamber P1a via the dialysate supplying line L1. On the other hand, when the plunger 2 is moved by the motor M toward the left in FIG. 4, the dialysate is supplied to the blood purification apparatus 15 from the supply liquid-side pumping chamber P1. Simultaneously, the diaphragm 8 is also pushed and thus deflected toward the left. This increases the volume of the supply liquid-side sub-pumping chamber P1a. Thus, part of the dialysate supplied to the blood purification apparatus 15 is absorbed or supplemented by the supply liquid-side sub-pumping chamber P1a.

Figure 5:
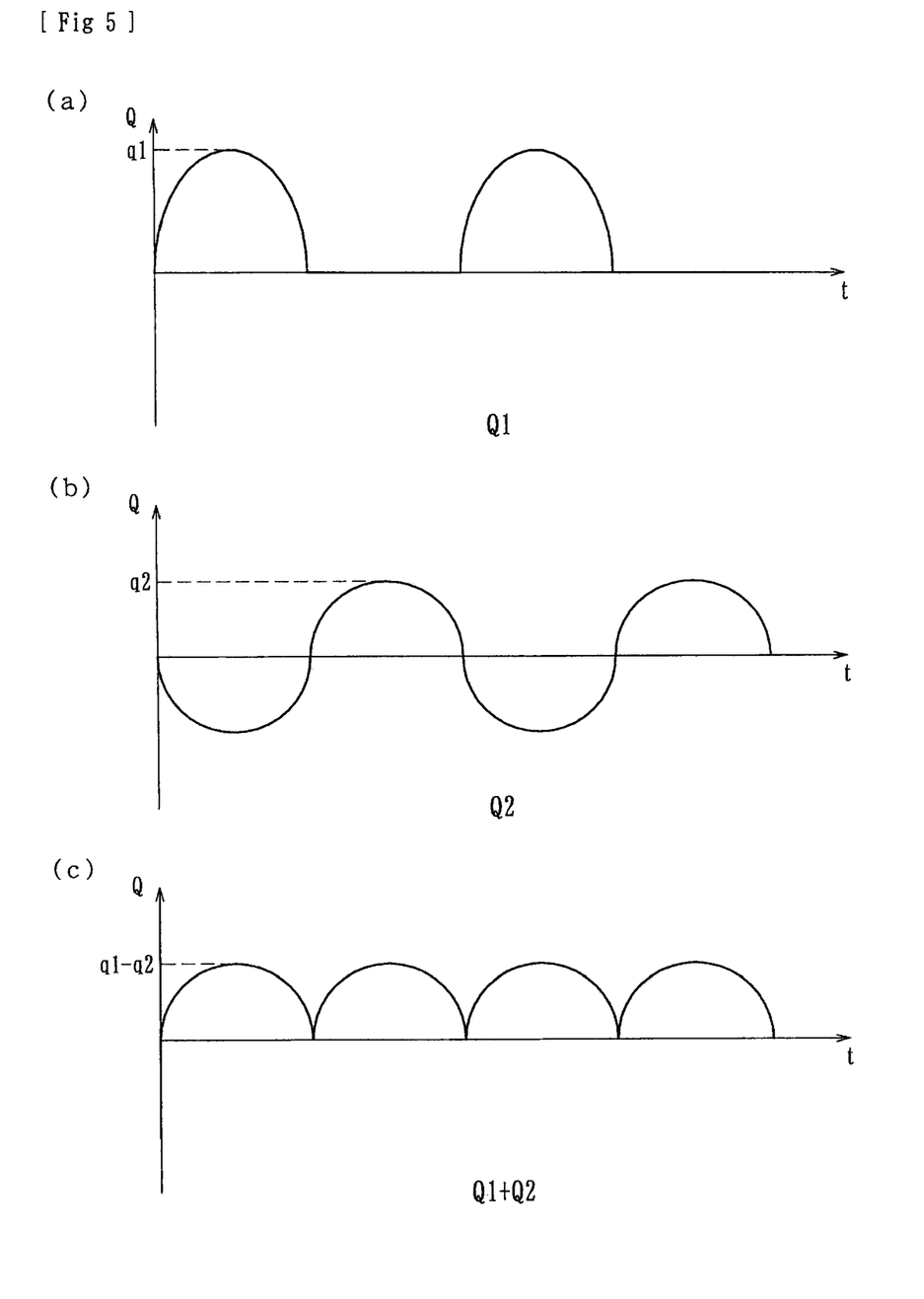

In the first condition of connection, the pulsation, a variation of flow rate per unit lapse of time, of a discharged flow from the supply liquid-side pumping chamber P1 and the pulsation of a sucked flow into the waste liquid-side pumping chamber P2 have a flow rate waveform illustrated in FIG. 5(a). The flow rate in the flow route L4 and the flow rate in the flow route L5 are respectively defined as Q1. On the other hand, the pulsation of a discharged flow from the supply liquid-side sub-pumping chamber P1a and a discharged flow from the waste liquid-side sub-pumping chamber P2a have a flow rate waveform shown in FIG. 5(b). The discharged flow rates from these chambers P1a, P2a are defined as Q2. The actual pulsations in the dialysate supplying line L1 and the dialysate discharge line L2 are determined as a synthesis of these pulsations in FIGS. 5(a) and 5(b) and illustrated in FIG. 5(c). As can be understood, the synthesized pulsation, amplitude in FIG. 5(c), is reduced.

The reciprocating motion of the plunger 2 supplies the dialysite to the blood purification apparatus 15 through the supply liquid-side pumping chamber P1 and the supply liquid-side sub-pumping chamber P1a. Also, the motion of the plunger 2 discharges the waste dialysate from the blood purification apparatus 15 to the outside through the waste liquid-side sub-pumping chamber P2a and the waste liquid-side sub-pumping chamber P2. Thus, it is possible to reduce the pulsation of the dialysate or waste dialysate caused by the reciprocating motion of the plunger 2. Especially under the first condition of connection, it is possible to reduce the pulsation during the supply and discharge of the dialysate to and from the blood purification apparatus 15. Thus, this prevents the purification membrane of the blood purification apparatus 15 from being damaged.

According to the present disclosure, if the discharging volumes of the supply liquid-side pumping chamber P1 and the waste liquid-side pumping chamber P2 are set about twice those of the supply liquid-side sub-pumping chamber P1a and the waste liquid-side sub-pumping chamber P2a, the pulsation caused during the supply of dialysate from the reciprocation pump to the blood purification apparatus 15 can be reduced. In this case the pulsation will be reduced if the discharging volumes of the supply liquid-side pumping chamber P1 and the waste liquid-side pumping chamber P2 are set larger than those of the supply liquid-side sub-pumping chamber P1a and the waste liquid-side sub-pumping chamber P2a.

Figure 6:
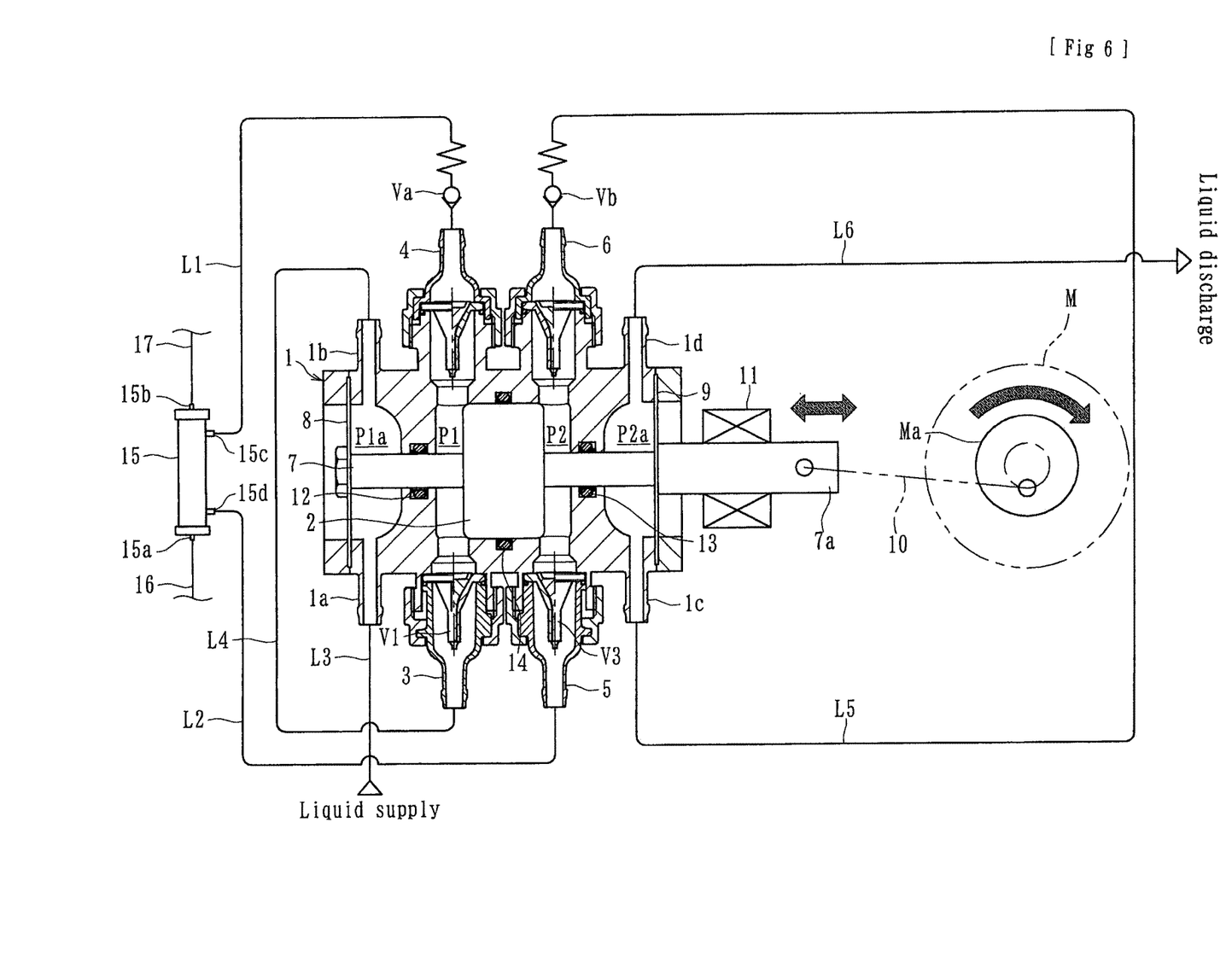
FIG. 6 is a schematic view showing a connection (second condition of connection) between the reciprocation pump and the blood purification apparatus.

In place of the first condition of connection, it is possible, as shown in FIG. 6, to connect the dialysate supplying line L1 between the dialysate inlet port 15c of the blood purification apparatus 15 and the supply liquid-side outlet port 4. Also, it is possible to connect the dialysate discharge line L2 between the dialysate discharging port 15d of the blood purification apparatus 15 and the waste liquid-side inlet port 5. This connection is hereinafter referred to as "second condition of connection.

In the second condition of connection, a flow route L4, forming part of the dialysate supplying line L1, is connected between the projected connection port 1b and the supply liquid-side inlet port 3. The projected connection port 1a is connected to a flow route L3 that forms part of the dialysate supplying line L1. The flow route L3 is further connected to the supplying source (not shown) of the dialysate conditioned to a predetermined concentration. Thus, the dialysate fed from the supplying source can be supplied to the blood purification apparatus 15 through the supply liquid-side sub-pumping chamber P1a and the supply liquid-side pumping chamber P1.

On the other hand, a flow route L5, forming part of the dialysate discharge line L2, is connected to the waste liquid-side outlet port 6 and the projected connection port 1c. The projected connection port 1d is connected to a flow route L6 that forms part of the dialysate discharge line L2. The flow route L6 is connected to any discharged liquid recovering means (not shown). Thus, the discharged liquid from the blood purification apparatus 15 can be recovered by the discharged liquid recovering means through the waste liquid-side pumping chamber P2 and the waste liquid-side sub-pumping chamber P2a.

In the second condition of connection, the pulsation, a variation of flow rate per unit lapse of time, has a flow rate waveform illustrated in FIG. 5(a). The flow rate in the flow route L4, flow rate of a sucked flow into the supply liquid-side pumping chamber P1, and the flow rate in the flow route L5, flow rate of a discharged flow from the waste liquid-side pumping chamber P2, is respectively defined as Q1. The pulsation has a flow rate waveform shown in FIG. 5(b). The sucked flow rates into the supply liquid-side sub-pumping chamber P1a and the waste liquid-side sub-pumping chamber P2a are defined as Q2. The pulsation in the flow routes L3, L6 is illustrated in FIG. 5(c), which is a synthesis of these pulsations in FIGS. 5(a) and 5(b). As can be understood, the synthesized pulsation is reduced, the amplitude in FIG. 5(c) is reduced as compared with those in FIGS. 5(a) and 5(b).

The reciprocating motion of the plunger 2 supplies the dialysite to the blood purification apparatus 15 through the supply liquid-side sub-pumping chamber P1a and the supply liquid-side pumping chamber P1. Additionally, the plunger motion discharges the waste dialysate from the blood purification apparatus 15 to the outside through the waste liquid-side pumping chamber P2 and the waste liquid-side sub-pumping chamber P2a. Thus, it is possible to reduce the pulsation of the dialysate or waste dialysate caused by the reciprocating motion of the plunger 2. Especially under the second condition of connection, it is possible to reduce the pulsation during the supply and discharge of the dialysate to and from the supply liquid-side sub-pumping chamber P1a. Also, it is possible to reduce the volume of a mixing chamber to be connected to the source of dialysate to obtain a desirable concentration of dialysate by mixing dense dialysate with water. Thus, this reduces the size of a blood purification apparatus.

Figure 7:
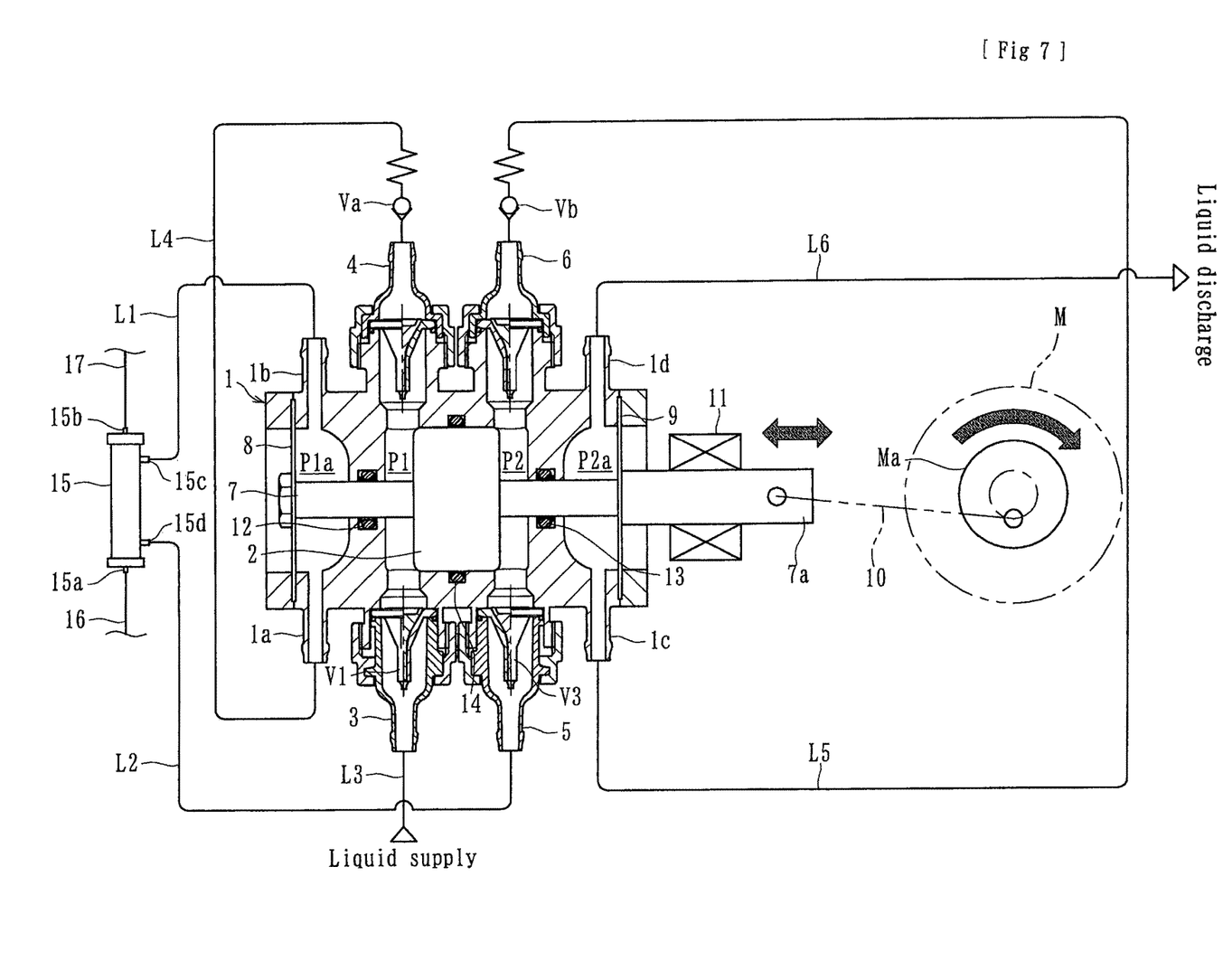
FIG. 7 is a schematic view showing a connection (third condition of connection) between the reciprocation pump and the blood purification apparatus.

Furthermore, in place of the first and second conditions of connection, it is possible, as shown in FIG. 7, to connect the dialysate supplying line L1 between the dialysate inlet port 15c of the blood purification apparatus 15 and the projected connection port 1b. Also, it is possible to connect the dialysate discharge line L2 between the dialysate discharging port 15d of the blood purification apparatus 15 and the waste liquid-side inlet port 5. This connection is hereinafter referred to as "third condition of connection".

In this third condition of connection, a flow route L4, forming part of the dialysate supplying line L1, is connected between the supply liquid-side outlet port 4 and the projected connection port 1a. The supply liquid-side inlet port 3 is connected to a flow route L3 that forms part of the dialysate supplying line L1. The flow route L3 is further connected to the supplying source (not shown) of the dialysate conditioned to a predetermined concentration. Thus, the dialysate fed from the supplying source can be supplied to the blood purification apparatus 15 through the supply liquid-side pumping chamber P1 and the supply liquid-side sub-pumping chamber P1a.

On the other hand, a flow route L5, forming part of the dialysate discharge line L2, is connected to the waste liquid-side outlet port 6 and the projected connection port 1c. The projected connection port 1d is connected to a flow route L6 that forms part of the dialysate discharge line L2. The flow route L6 is connected to any discharged liquid recovering means (not shown). Thus, liquid discharged from the blood purification apparatus 15 can be recovered by the discharged liquid recovering means through the waste liquid-side pumping chamber P2 and the waste liquid-side sub-pumping chamber P2a.

Figure 8:
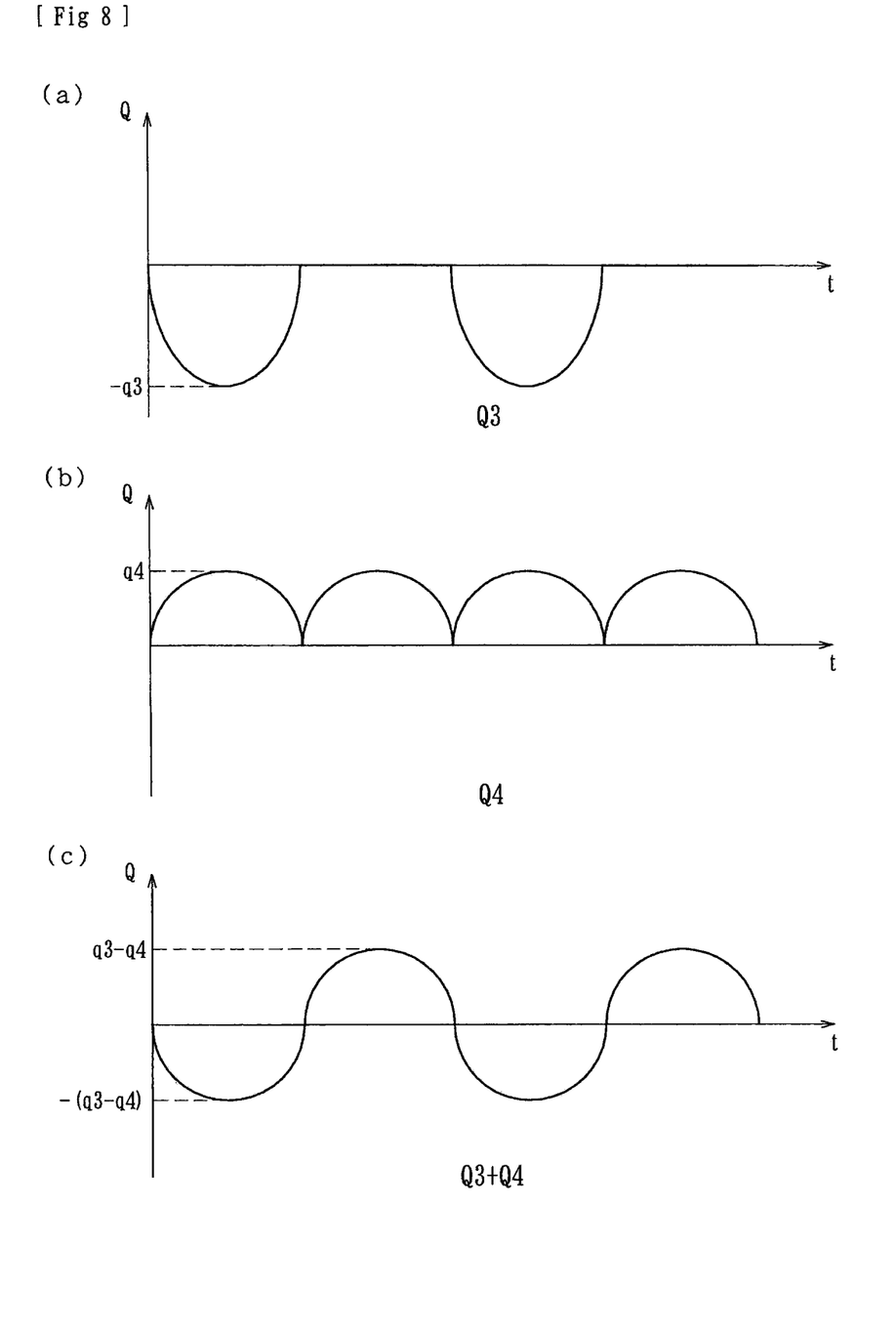

In the third condition of connection, a variation of flow rate per unit lapse of time, the pulsation, has a flow rate waveform illustrated in FIG. 8(a). The suction flow rate sucked into the waste liquid-side pumping chamber P2, flow rate of the dialysate discharge line L2, is defined as −Q3. The negative value means a flow rate discharged from the blood purification apparatus 15. On the other hand, the flow rate Q4 of the dialysate supplying line L1, synthesis of variation of flow rate in the supply liquid-side pumping chamber P1 and the supply liquid-side sub-pumping chamber, has a flow rate waveform illustrated in FIG. 8(b). The positive value means a flow rate supplied to the blood purification apparatus 14. The synthesis (Q3+Q4) of the variation of the flow rate exhibits the pulsation in the blood purification apparatus 15 as shown in FIG. 8(c). As can be understood, the pulsation is intentionally caused.

In the third condition of connection, the flow rate waveform of FIG. 8(c) can be obtained by differentiating the flow rate waveform from the supply liquid-side sub-pumping chamber P1a and the flow rate waveform into the waste liquid-side pumping chamber P2. The flow rate waveform from the supply liquid-side pumping chamber P1a is a repeating waveform of small pulsation. The flow rate waveform to the waste liquid-side pumping chamber P2 is a repeating waveform of presence and absence of flow. The flow rate of the dialysate flowing into the blood purification apparatus 15 and the flow rate of the waste dialysate flowing out from the blood purification apparatus 15 are same. The flow rate waveform of FIG. 8(c) enables to positively and intentionally perform the flow-in and flow-out of the dialysate through the blood purification membrane within the blood purification apparatus 15. In this case, it is possible to discharge the dialysate by connecting the dialysate supplying line L1 between the dialysate inlet port 15c and the supply liquid-side outlet port 4 as well as by connecting the dialysate discharge line L2 between the dialysate discharging port 15d and the projected connection port 1c. The dialysate is then passed through the waste liquid-side pumping chamber P2. In this case, the flow rate waveform may be reversed. Thus, in the third condition of connection, the flow rate waveform from the supply liquid-side pumping chamber P1 is a repeating waveform of presence and absence of flow. Also, the flow rate waveform to the waste liquid-side pumping chamber P2 is a repeating waveform of small pulsation.

As shown in the first, second and third conditions of connection, the order of flow of the dialysate is through the supply liquid-side pumping chamber P1 and the supply liquid-side sub-pumping chamber P1a. Also, the order of flow of the waste dialysate is through the waste liquid-side pumping chamber P2 and the waste liquid-side sub-pumping chamber P2a. The order of flow is arbitrarily selected to arbitrarily control pulsation caused by the reciprocating motion of the reciprocation mechanism. Thus, it is possible to set the pulsation at an arbitral position of the pump to have a desirable flow rate waveform.

That is, the flow-in and flow-out of the dialysate through the blood purification membrane within the blood purification apparatus 15 are repeated when the dialysate flows from the supply liquid-side pumping chamber P1 to the supply liquid-side sub-pumping chamber P1a as well as when the waste dialysate flows from the waste liquid-side sub-pumping chamber P2 to the waste liquid-side sub-pumping chamber P2a. Thus, it is possible to reduce the pulsation downstream of the waste liquid-side sub-pumping chamber P2a. On the other hand, the flow-in and flow-out of the dialysate through the blood purification membrane within the blood purification apparatus 15 are repeated when the dialysate flows from the supply liquid-side sub-pumping chamber P1a to the supply liquid-side pumping chamber P1 as well as when the waste dialysate flows from the waste liquid-side sub-pumping chamber P2a to the waste liquid-side pumping chamber P2. Accordingly, it is possible to reduce the pulsation upstream of the supply liquid-side sub pumping chamber P1a. Thus, it is possible to set the pulsation at an arbitral position of the pump to have a desirable flow rate waveform. The pulsation caused by the reciprocating motion of the plunger 2 can be arbitrarily controlled by arbitrarily selecting the condition of connection.

According to the present disclosure, the reciprocation pump is provided with the supply liquid-side sub-pumping chamber P1a and the waste liquid-side sub-pumping chamber P2a. In addition, it includes the supply liquid-side pumping chamber P1 and the waste liquid-side pumping chamber P2. Thus, the reciprocating motion of the reciprocation mechanism enables the liquid to be supplied to the blood purification apparatus 15 through the supply liquid-side pumping chamber P1 and the supply liquid-side sub-pumping chamber P1a. Additionally, it enables the waste liquid from the blood purification apparatus 15 to be discharged to the outside through the waste liquid-side pumping chamber P2 and the waste liquid-side sub-pumping chamber P2a. Thus, it is possible to reduce the pulsation of the liquid and waste liquid caused by the reciprocating motion of the reciprocation mechanism.

The reciprocation pump includes the rod 7 extending through the supply liquid-side sub-pumping chamber P1a, the supply liquid-side pumping chamber P1, the waste liquid-side pumping chamber P2 and the waste liquid-side sub-pumping chamber P2a. The rod 7 is connected to the plunger 2 and the motor M. The rod 7 transmits a driving force of the motor M to the plunger 2. Diaphragms 8, 9, respectively, are mounted on the distal end and the proximal end of the rod 7. The diaphragms 8, 9, along with the case 1, form the supply liquid-side sub-pumping chamber P1a and the waste liquid-side sub-pumping chamber P2a, respectively. Thus, it is possible to construct the supply liquid-side sub-pumping chamber P1a to be interlocked with the plunger 2 to vary its volume reversely to that of the volume variation of the supply liquid-side pumping chamber P1. Also, the waste liquid-side sub-pumping chamber P2a is interlocked with the plunger 2 to vary its volume reversely to that of the volume variation of the waste liquid-side pumping chamber P2. In addition, it eliminates any separate sealing means such as shaft seals at mounting portions of the diaphragms 8, 9.

The reciprocation mechanism includes the plunger 2 formed on the rod 7 to form, along with the casing 1, the supply liquid-side pumping chamber P1 and the waste liquid-side pumping chamber P2. Thus, it is possible to use a conventional plunger and to reduce the manufacturing cost. The supply liquid-side sub-pumping chamber P1a and the waste liquid-side sub-pumping chamber P2a are arranged, respectively, adjacent to the supply liquid-side pumping chamber P1 and the waste liquid-side pumping chamber P2 at their external side. Sealing elements 12, 13 are arranged, respectively, in walls through which the rod 7 extends to partition the supply liquid-side pumping chamber P1 and the supply liquid-side sub-pumping chamber P1a as well as the waste liquid-side pumping chamber P2 and the waste liquid-side sub-pumping chamber P2a. Thus, it is possible to prevent the dialysate, to be supplied to the blood purification apparatus 15, as well as the waste dialysate, from the blood purification apparatus 15, from leaking to the outside of the reciprocation pump.

In addition, a central sealing element 14 is arranged between the supply liquid-side pumping chamber P1 and the waste liquid-side pumping chamber P2. The sealing element 14 is substantially at the reciprocating center of the plunger 2. The sealing element 14 seals the supply liquid-side pumping chamber P1 and the waste liquid-side pumping chamber P2 from each other. The leaked dialysate can flow from the supply liquid-side pumping chamber P1 to the waste liquid-side pumping chamber P2. The leaked waste dialysate can flow from the waste liquid-side pumping chamber P2 to the supply liquid-side pumping chamber P1. Thus, it is possible to prevent the leaked dialysate and waste dialysate from leaking to the outside of the reciprocation pump.

Figure 9:
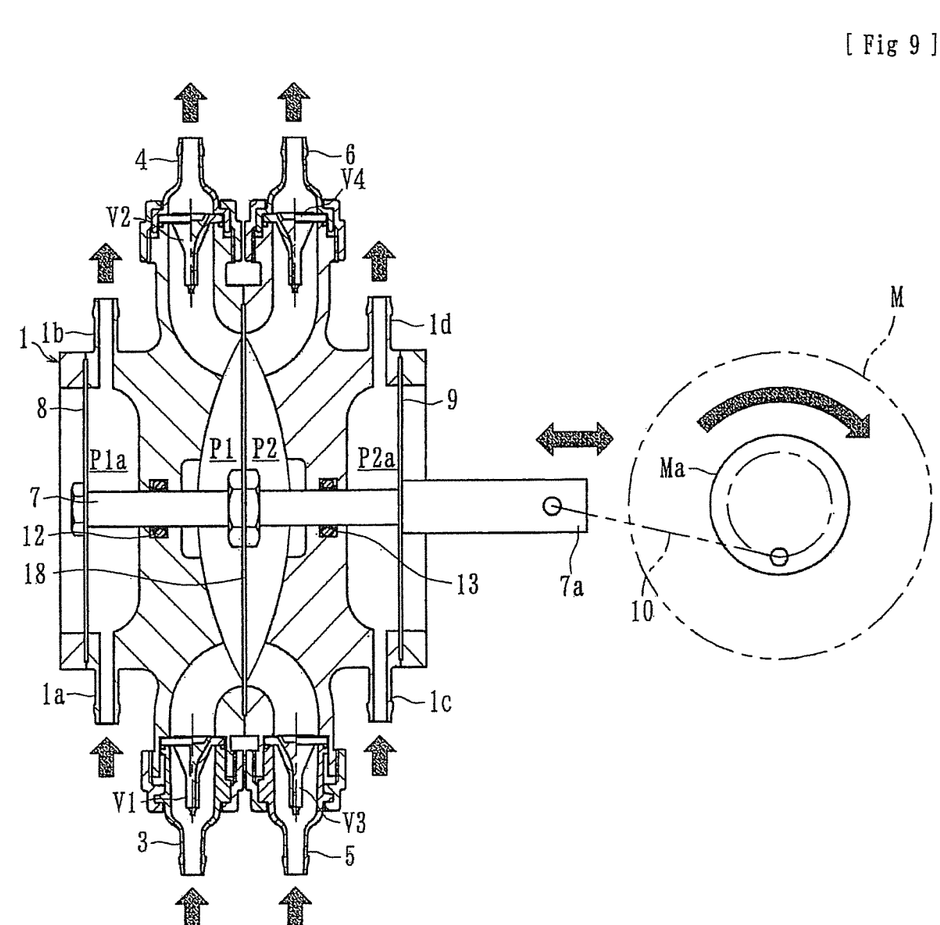
FIG. 9 is a longitudinal-section view of a reciprocation pump of another embodiment of the present disclosure.

FIG. 9 illustrates another embodiment of the present disclosure. Here, a diaphragm 18, in place of the plunger 2, is mounted on the rod 7 to form the supply liquid-side pumping chamber P1 and the waste liquid side pumping chamber P2. Also, in this embodiment, the supply liquid-side sub-pumping chamber P1a and the waste liquid-side sub-pumping chamber P2a are arranged, respectively, adjacent to the supply liquid-side pumping chamber P1 and the waste liquid-side pumping chamber P2 at their external side. Sealing elements 12, 13 are arranged, respectively, in walls through which the rod 7 extends to partition the supply liquid-side pumping chamber P1 and the supply liquid-side sub-pumping chamber P1a as well as the waste liquid-side pumping chamber P2 and the waste liquid-side sub-pumping chamber P2a. Thus, it is possible to prevent the dialysate, to be supplied to the blood purification apparatus 15, as well as the waste dialysate, from the blood purification apparatus 15, from leaking to the outside of the reciprocation pump. Furthermore in this embodiment, the reciprocation mechanism includes the diaphragm 18. Thus, it is possible to eliminate the central sealing element 14 to sealingly form the supply liquid-side pumping chamber P1 and the waste liquid-side pumping chamber P2 as in the above case using the plunger 2 for this purpose.

Furthermore, the present disclosure is not limited to a reciprocation pump used to supply dialysate to the blood purification apparatus 15. The disclosure can be applied to other reciprocation mechanisms, industrial pumps used for common use, that supply liquids to other objective apparatus other than the blood purification apparatus. Thus, it is possible to reduce the pulsation of the liquid and waste liquid caused by the reciprocating motion of the reciprocation mechanism by providing the reciprocation pump with the supply liquid-side sub-pumping chamber and the waste liquid-side sub-pumping chamber in addition to the supply liquid-side pumping chamber and the waste liquid-side pumping chamber. Accordingly, the reciprocating motion of the reciprocation mechanism enables the liquid to be supplied to the objective apparatus through the supply liquid-side pumping chamber and the supply liquid-side sub-pumping chamber. Also, the motion enables the waste liquid from the objective apparatus to be discharged to the outside through the waste liquid-side pumping chamber and the waste liquid-side sub-pumping chamber.

The present disclosure can be applied to a reciprocation pump and a dialysis apparatus equipped with such a reciprocation pump with a different external appearance from that shown in the accompanied drawings or having additional functions. The reciprocation pump includes a supply liquid-side sub-pumping chamber to contain and send out liquid adapted to be communicated with the supply liquid-side pumping chamber. Also, the liquid-side sub-pumping chamber is interlocked with the reciprocation mechanism to vary its volume reversely to that of the volume variation of the supply liquid-side pumping chamber. A waste liquid-side sub-pumping chamber contains and sends out liquid adapted to communicate with the waste liquid-side pumping chamber. The waste liquid-side sub-pumping chamber is interlocked with the reciprocation mechanism to vary its volume reversely to that of the volume variation of the waste liquid-side pumping chamber. The reciprocating motion of the reciprocation mechanism enables the liquid to be supplied to the objective apparatus through the supply liquid-side pumping chamber and the supply liquid-side sub-pumping chamber. Also, it enables the waste liquid from the objective apparatus to be discharged to the outside through the waste liquid-side pumping chamber and the waste liquid-side sub-pumping chamber.

The present disclosure has been described with reference to the preferred embodiment. Obviously, modifications and alternations will occur to those of ordinary skill in the art upon reading and understanding the preceding detailed description. It is intended that the present disclosure be construed as including all such alternations and modifications insofar as they come within the scope of the appended claims or their equivalents.

What is claimed is:
1. A reciprocation pump comprising:
a housing;
a supply liquid-side pumping chamber for supplying a liquid from a source to an objective apparatus, the supply liquid-side pumping chamber in the housing;
a waste liquid-side pumping chamber for discharging a waste liquid discharged from the objective apparatus to the outside, the waste liquid-side pumping chamber in the housing;
a reciprocation mechanism reciprocates between the supply liquid-side pumping chamber and the waste liquid-side pumping chamber in the housing, a member on the reciprocation mechanism in the housing separating the supply liquid side pumping chamber from the waste liquid side pumping chamber, reciprocating motion of the reciprocation mechanism, via the member, performs suction and discharge of the liquid to and from the supply liquid-side pumping chamber as well as suction and discharge of the waste liquid to and from the waste liquid-side pumping chamber;
a driving source for driving the reciprocation mechanism;
the reciprocation pump is adapted to supply the liquid from the source to the objective apparatus with the supply liquid-side pumping chamber and to discharge the waste liquid from the objective apparatus with the waste liquid-side pumping chamber to the outside;
the reciprocation pump further comprises a rod and at least two diaphragms, the rod connecting the reciprocation mechanism and the driving source and transmitting a driving force of the driving source to the reciprocation mechanism, each of the at least two diaphragms, respectively, mounted one on a distal end and one on a proximal end of the rod forming the supply liquid-side sub-pumping chamber and the waste liquid-side sub-pumping chamber, respectively, the at least two diaphragms both configured to be secured to the housing by a peripheral edge fit into the housing in a sealed manner and each of the at least two diaphragms is displaced with its peripheral edge secured to the housing as the rod moves, the at least two diaphragms, respectively, are deflected so that the volume of the supply liquid-side sub-pumping chamber and the volume of the waste liquid-side sub-pumping chamber can be varied, respectively:
a supply liquid-side sub-pumping chamber for containing and sending out liquid adapted to be communicated with the supply liquid-side pumping chamber and interlocked with the reciprocation mechanism to vary its volume reversely to that of the volume variation of the supply liquid-side pumping chamber, the supply liquid-side pumping chamber and the supply liquid-side sub-pumping chamber arranged only in series so that the supply liquid entering the objective apparatus, in a first condition, piping is arranged so that supply fluid passes first into and through the supply liquid-side sub-pumping chamber or, in a second separate and discreet condition, piping is arranged so that supply fluid passes first into and through the supply liquid-side pumping chamber such that when the reciprocation mechanism reciprocates and performs suction and discharge of the supply liquid, the supply liquid always passes through both the supply liquid-side sub-pumping chamber and the supply liquid-side pumping chamber, respectively, before entering into the objective apparatus;
a waste liquid-side sub-pumping chamber for containing and sending out liquid adapted to be communicated with the waste liquid-side pumping chamber and interlocked with the reciprocation mechanism to vary its volume reversely to that of the volume variation of the waste liquid-side pumping chamber, the waste liquid-side pumping chamber and the waste liquid-side sub-pumping chamber arranged only in series so that the waste liquid exiting the objective apparatus, in a first condition, piping is arranged so that waste liquid exits first into and through the waste liquid-side pumping chamber or, in a second separate and discreet condition, piping is arranged so that waste liquid passes first into and through the waste liquid-side sub-pumping chamber such that when the reciprocation mechanism reciprocates and performs suction and discharge of the waste liquid, the waste liquid always passes through both the waste liquid-side pumping chamber and the waste liquid-side sub-pumping chamber, respectively, to the outside; and the reciprocating motion of the reciprocation mechanism enables liquid to be supplied to the objective apparatus through both the supply liquid-side pumping chamber and the supply liquid-side sub-pumping chamber as well as enables the waste liquid to be discharged from the objective apparatus to the outside through both the waste liquid-side pumping chamber and the waste liquid-side sub-pumping chamber and the supply liquid-side pumping chamber and waste liquid-side pumping chamber are larger than the supply liquid-side sub-pumping chamber and waste liquid-side sub-pumping chamber, respectively, so that an order of flow of the supply fluid through the supply liquid-side pumping chamber and the supply liquid-side sub-pumping chamber and/or order of flow of the waste liquid through the waste liquid-side pumping chamber and the waste liquid-side sub-pumping chamber are selected to control pulsation caused by the reciprocating motion of the reciprocation mechanism.

2. The reciprocation pump of claim 1, wherein the reciprocation member comprises a plunger formed on the rod to form the supply liquid-side pumping chamber and the waste liquid-side pumping chamber.

3. The reciprocation pump of claim 1, wherein the reciprocation member comprises a diaphragm mounted on the rod to form the supply liquid-side pumping chamber and the waste liquid-side pumping chamber.

4. The reciprocation pump of claim 1, wherein the objective apparatus is a blood purification apparatus and the liquid is dialysate.

5. A dialysis apparatus equipped with the reciprocation pump of claim 4.

6. A reciprocation pump comprising:
a housing;
a supply liquid-side pumping chamber for supplying a liquid from a source to an objective apparatus, the supply liquid-side pumping chamber in the housing;
a waste liquid-side pumping chamber for discharging a waste liquid discharged from the objective apparatus to the outside, the waste liquid-side pumping chamber in the housing;
a first flow line for connecting the supply source with a supply source side of the objective apparatus for supplying the liquid in a first direction from the supply source to the objective apparatus;
a second flow line for connecting a discharge liquid recovering mechanism side of the objective apparatus with the outside for discharging liquid in a second direction from the objective apparatus to the outside;
a reciprocation mechanism reciprocates between the supply liquid-side pumping chamber and the waste liquid-side pumping chamber in the housing, a member on the reciprocation mechanism in the housing separating the supply liquid-side pumping chamber from the waste liquid-side pumping chamber, reciprocating motion of the reciprocation mechanism, via the member, performs suction and discharge of the liquid to and from the supply liquid-side pumping chamber as well as suction and discharge of the waste liquid to and from the waste liquid-side pumping chamber;

a driving source for driving the reciprocation mechanism;

the reciprocation pump is adapted to supply the liquid from the source to the objective apparatus with the supply liquid-side pumping chamber and to discharge the waste liquid from the objective apparatus with the waste liquid-side pumping chamber to the outside;

the reciprocation pump further comprises:

a supply liquid-side sub-pumping chamber for containing and sending out liquid adapted to be communicated with the supply liquid-side pumping chamber and interlocked with the reciprocation mechanism to vary its volume reversely to that of the volume variation of the supply liquid-side pumping chamber, the supply liquid-side pumping chamber and the supply liquid-side sub-pumping chamber arranged only in series so that the supply liquid entering the objective apparatus, in a first condition, piping is arranged so that supply fluid passes first into and through the supply liquid-side sub-pumping chamber or, in a second separate and discreet condition, piping is arranged so that supply fluid passes first into and through the supply liquid-side pumping chamber such that when the reciprocation mechanism reciprocates and performs suction and discharge of the supply liquid, the supply liquid always passes through both the supply liquid-side sub-pumping chamber and the supply liquid-side pumping chamber, respectively, before entering into the objective apparatus and the supply liquid-side pumping chamber or the supply liquid-side sub-pumping chamber being positioned in the first flow line and pumping chamber and supply liquid-side the supply liquid-side subpumping chamber connecting to each other, the first flow line, connected to the supplying source side of the objective apparatus, is provided in either of the supply liquid-side pumping chamber or the supply liquid-side sub-pumping chamber;

a waste liquid-side sub-pumping chamber for containing and sending out liquid adapted to be communicated with the waste liquid-side pumping chamber and interlocked with the reciprocation mechanism to vary its volume reversely to that of the volume variation of the waste liquid-side pumping chamber, the waste liquid-side pumping chamber and the waste liquid-side sub-pumping chamber arranged in only series so that the waste liquid exiting the objective apparatus, in a first condition, piping is arranged so that waste liquid exits first into and through the waste liquid-side pumping chamber or, in a second separate and discreet condition, piping is arranged so that waste liquid passes first into and through the waste liquid-side sub-pumping chamber such that when the reciprocation mechanism reciprocates and performs suction and discharge of the waste liquid, the waste liquid always passes through both the waste liquid-side pumping chamber and the waste liquid-side sub-pumping chamber, respectively, to the outside, the waste liquid-side pumping chamber and the waste liquid-side sub-pumping chamber are positioned in the second flow line and the waste liquid-side pumping chamber and the waste liquid-side sub-pumping chamber connecting to each other, the second flow line, connected to the discharged liquid recovering mechanism side of the objective apparatus, is provided in either of the waste liquid-side pumping chamber or the waste liquid-side sub-pumping chamber; and each reciprocating motion of the reciprocation mechanism enables liquid to be supplied to the objective apparatus by always passing through both the supply liquid-side pumping chamber and the supply liquid-side sub-pumping chamber as well as enables the waste liquid to be discharged from the objective apparatus to the outside by always passing through both the waste liquid-side pumping chamber and the waste liquid-side sub-pumping chamber and the supply liquid-side pumping chamber and waste liquid-side pumping chamber are larger than the supply liquid-side sub-pumping chamber and waste liquid-side sub-pumping chamber, respectively, so that an order of flow through the supply liquid-side pumping chamber and the supply liquid-side sub-pumping chamber and/or order of flow through the waste liquid-side pumping chamber and the waste liquid-side sub-pumping chamber are selected to control pulsation caused by the reciprocating motion of the reciprocation mechanism.

7. The reciprocation pump of claim 6, wherein the reciprocation pump further comprises:

a rod extending through the supply liquid-side sub-pumping chamber, the supply liquid-side pumping chamber, the waste liquid-side pumping chamber and the waste liquid-side sub-pumping chamber, the rod connected to the reciprocation mechanism and the driving source to transmit a driving force of the driving source to the reciprocation mechanism; and diaphragms, respectively, mounted on a distal end and a proximal end of the rod to form the supply liquid-side sub-pumping chamber and the waste liquid-side sub-pumping chamber, respectively.

8. The reciprocation pump of claim 7, wherein the reciprocation member comprises a plunger formed on the rod to form the supply liquid-side pumping chamber and the waste liquid-side pumping chamber.

9. The reciprocation pump of claim 7, wherein the reciprocation member comprises a diaphragm mounted on the rod to form the supply liquid-side pumping chamber and the waste liquid-side pumping chamber.

10. The reciprocation pump of claim 6, wherein the objective apparatus is a blood purification apparatus and the liquid is dialysate.

11. A dialysis apparatus equipped with the reciprocation pump of claim 10.

* * * * *